United States Patent
Trygstad

(10) Patent No.: US 9,903,810 B2
(45) Date of Patent: Feb. 27, 2018

(54) METHOD AND APPARATUS FOR ANALYSIS OF ALKYLATION CATALYST COMPOSITION

(71) Applicant: Yokogawa Corporation of America, Newnan, GA (US)

(72) Inventor: William Marcus Trygstad, Spring, TX (US)

(73) Assignee: Yokogawa Corporation of America, Newnan, GA (US)

( * ) Notice: Subject to any disclaimer, the term of this patent is extended or adjusted under 35 U.S.C. 154(b) by 404 days.

(21) Appl. No.: 14/544,490

(22) Filed: Jan. 12, 2015

(65) Prior Publication Data
US 2015/0198538 A1    Jul. 16, 2015

Related U.S. Application Data

(60) Provisional application No. 61/964,769, filed on Jan. 14, 2014.

(51) Int. Cl.
| G01N 21/85 | (2006.01) |
| G01N 21/359 | (2014.01) |
| G01N 21/65 | (2006.01) |
| G01N 21/3577 | (2014.01) |

(52) U.S. Cl.
CPC ....... *G01N 21/359* (2013.01); *G01N 21/3577* (2013.01); *G01N 21/65* (2013.01)

(58) Field of Classification Search
None
See application file for complete search history.

(56) References Cited

U.S. PATENT DOCUMENTS

| 3,794,691 | A | * | 2/1974 | Dixon | .................... B01J 31/143 |
| | | | | | 585/452 |
| 5,264,650 | A | * | 11/1993 | Better | ..................... C01B 7/195 |
| | | | | | 585/723 |
| 5,681,749 | A | | 10/1997 | Ramamoorthy | |
| 6,096,553 | A | | 8/2000 | Heald et al. | |
| 6,228,650 | B1 | | 5/2001 | Moore et al. | |
| 6,387,705 | B1 | | 5/2002 | Claibourn et al. | |
| 7,972,863 | B2 | | 7/2011 | Trygstad et al. | |
| 8,211,706 | B2 | | 7/2012 | Trygstad et al. | |
| 8,334,142 | B2 | | 12/2012 | Trygstad et al. | |
| 8,751,167 | B2 | | 6/2014 | Trygstad | |
| 8,895,314 | B2 | * | 11/2014 | Trygstad | .............. G01N 21/359 |
| | | | | | 436/94 |

(Continued)

OTHER PUBLICATIONS

Thomas S. Bianchi and Elizabeth A. Canuel in Chemical Biomarkers in Aquatic Ecosystems, Copyright_c 2011 by Princeton University Press, 417 pages.*

(Continued)

*Primary Examiner* — Tung Lau
(74) *Attorney, Agent, or Firm* — Davis, Malm & D'Agostine, P.C.

(57) ABSTRACT

Apparatus and method for the determination of weight fractions of hydrocarbons, water and acid in the acid catalyst phase of petroleum refinery alkylation catalyst streams by flowing the acid catalyst phase through a density detector and a spectrometer cell so that the determination can be made according to first principles. An alternative apparatus and method uses spectroscopy without the density detector.

9 Claims, 7 Drawing Sheets

(56) References Cited

U.S. PATENT DOCUMENTS

2003/0158457 A1* 8/2003 Gershuni ............... B01J 19/088
585/719
2011/0111509 A1 5/2011 Trygstad et al.

OTHER PUBLICATIONS

E. Hywel Evans in Atomic spectrometry update. Advances in atomic emission, absorption and fluorescence spectrometry, and related techniques, First published as an Advance Article on the web May 26, 2006, 34 pages.*
A. L. Burlingame in Mass Spectrometry, in Analytical Chemistry, vol. 70, No. 16, Aug. 15, 1998, 70 pages.*
Intermational Search Report and Written opinion in the corresponding PCT application PCT/US2015/000002, dated Apr. 30, 2015.

* cited by examiner

METHOD AND APPARATUS FOR ANALYSIS OF ALKYLATION CATALYST COMPOSITION

This application claims priority to U.S. Provisional Patent Application Ser. No. 61/964,769 filed Jan. 14, 2014.

BACKGROUND OF THE INVENTION

The instant invention is in the field of methods and apparatus for online analysis of liquid process streams in petroleum refineries and more specifically the instant invention is in the field of methods and apparatus for determining the composition of alkylation catalyst comprising a single phase mixture consisting of strong acid such as hydrofluoric acid (HF) or sulfuric acid ($H_2SO_4$, or SA), water (H2O), and hydrocarbons (HC) that include acid soluble oil (ASO), isobutane, alkylate, and the like.

The use of multivariable methods to analyze HF alkylation catalyst, and the motivation to do so, is well known (see U.S. Pat. Nos. 5,681,749; 6,096,553; 7,972,863; 8,211,706; 8,334,142 or 8,751,167). For example, chemometrics have been applied to obtain predictions of % HF, % $H_2O$, and % ASO from spectra measured by online near-infrared (NIR) and Raman spectrometers. Also, multilinear regression (MLR) methods have been used to infer the same properties using outputs from a plurality of univariate sensors integrated into a single analyzer system. These technologies have provided three principal benefits to refiners. First, they reduce the frequency with which samples must be manually obtained from the process and analyzed in the refinery laboratory. Second, the frequency of analysis is practically continuous in contrast to the intermittent lab measurements. But as important as are these two benefits in consideration of the objective to control and optimize alkylation unit operation, minimizing operator exposure is a benefit of paramount concern where the alkylation catalyst contains HF. Due to its toxicity, refiners have long sought means for reliable online analysis so as to minimize the need for operators to obtain samples manually and for the subsequent manual analysis in the refinery laboratory. Reliability concerns both the accuracy of the analytical output and the amount of maintenance required to keep the analyzer system operational.

As regards accuracy, both the spectrometric and the multi-sensor approaches share a common inability to compensate for the effects of variable composition of hydrocarbons in the catalyst (HC). Though wishing to not be bound by any particular understanding of alkylation catalyst chemistry, it is believed that HC comprises a continuum of compounds ranging from isobutane to heavy ASO, the latter consisting of pre-polymers whose molecular weights may be greater than 1000. (In industry parlance, ASO is sometimes referred to as polymer.) The HC between those extremes may include light ASO and perhaps even some alkylate. Rather than having a nominally constant composition, the proportions of these HC components can change as a function of feed quality and operating conditions. Such variation can affect two properties that limit the accuracy of prior art approaches for analyzing HF-containing catalyst (HF catalyst). First, the aggregate density of HC has been estimated to vary by more than about ±10% from a nominal value thought to be typically in the range of about 0.78-0.82 kg/L. Second, the hydrogen-to-carbon ratio (H:C) can decrease as the aggregate density of the hydrocarbons increases, the relative variation estimated as being similar to that for density, e.g. about ±10%. The former can have a proportionate impact on measurement accuracy in the case of a multi-sensor analyzer that assumes HC density is nominally constant. Even worse, the effects of the two types of variation in HC compound each other in chemometric-based NIR and Raman methods, which also are sensitive to the amounts and types of chemical functionality in HC compounds.

Concerning operational reliability, NIR-based HF analyzer systems available to refiners have sampling subsystems that are somewhat complex and unreliable insofar as they employ tubing and numerous fittings that are susceptible to corrosion and eventually to leakage and also contain at least one automated valve that must be replaced at regular intervals due to seal wear caused by repeated open/close cycling. Furthermore, the practice of enclosing the sampling system in a temperature-controlled cabinet demands layers of safety measures to warn against possible leakage of HF and its accumulation to dangerous levels within the enclosure. Consequently, refiners are not wholly satisfied with extant prior art systems for online analysis of acid catalyst despite the ostensible benefits.

SUMMARY OF THE INVENTION

The instant invention is an advancement over the above-mentioned art. In one embodiment, the instant invention is apparatus for online determination of the weight fractions of acid, water, and hydrocarbons in the acid catalyst phase of an alkylation process liquid, the process liquid comprising a liquid phase consisting primarily of hydrocarbon and a liquid phase consisting primarily of the acid catalyst, where said phases are distinct and substantially immiscible. The apparatus comprises: a liquid flow path configured to convey the continuously flowing process liquid from an alkylation process to a liquid-liquid separator for separating the liquid hydrocarbon phase from the liquid acid catalyst phase; a liquid flow path for flowing the acid catalyst phase through a density detector for measuring the density of the acid catalyst phase ($d_{cat}$) and also through an optical flow cell in optical communication with a spectrometer for measuring the spectrum of the acid catalyst; and a processor that is configured to capture data from the density detector and spectra from the spectrometer, and is programmed to manipulate each spectrum to determine net responses in the same for the acid ($R_A$) and for water ($R_{H_2O}$) and to determine the weight fractions of acid, water, and hydrocarbons in the acid catalyst phase ($X_A$, $X_{H_2O}$, and $X_{HC}$ respectively) according to the following equations derived hereinbelow, $$X_{HF} = k'_A \cdot \frac{R_A}{d_{cat}}$$

$$X_{H_2O} = k'_{H_2O} \cdot \frac{R_{H_2O}}{d_{cat}}$$

$$X_{HC} = 1 - X_A - X_{H_2O}$$

where $k'_A$ and $k'_{H_2O}$ are constants determined by calibration based on acid catalyst mixtures whose concentrations of the acid and water, respectively, are known. The acid is typically hydrofluoric acid or sulfuric acid. The processor is typically a general purpose digital computer. The density sensor is typically a Coriolis density detector.

In another particular embodiment of the present invention, the spectrometer is a Raman spectrometer, the optical flow cell is a Raman cell, the net response in the acid catalyst spectrum for the acid ($R_A$) is the net intensity in the Raman spectrum of the acid catalyst for the acid, and the net response in the acid catalyst spectrum for water ($R_{H_2O}$) is the net intensity in the Raman spectrum of the acid catalyst for water.

In another, particularly favorable embodiment of the present invention, the spectrometer is a near-infrared spectrometer, the optical cell is a near-infrared transmission cell, and the processor is configured to capture data from the density detector and NIR spectra from the spectrometer and is programmed to manipulate each NIR spectrum to determine net absorbances in the same for the acid ($A_A$) and for water ($A_{H_2O}$) and to determine the weight fractions of acid and water in the acid catalyst phase ($X_A$, $X_{H_2O}$, respectively) according to the following equations, $$X_A = k_A \cdot \frac{A_A}{d_{cat}}$$

$$X_{H_2O} = k_{H_2O} \cdot \frac{A_{H_2O}}{d_{cat}}$$

where $k_A$ and $k_{H_2O}$ are constants determined by calibration based on acid catalyst mixtures whose concentrations of the acid and water, respectively, are known. Again, $X_{HC}$ is calculated as $X_{HC}=1-X_A-X_{H_2O}$. The acid is typically hydrofluoric acid or sulfuric acid. The processor is typically a general purpose digital computer. The density sensor is typically a Coriolis density detector.

In another embodiment, the instant invention is apparatus for online determination of the weight fractions of acid, water, and hydrocarbons in the acid catalyst phase of an alkylation process liquid, the process liquid comprising a liquid phase consisting primarily of hydrocarbon and a liquid phase consisting primarily of the acid catalyst, where said phases are distinct and substantially immiscible. The apparatus comprises: a liquid flow path configured to convey the process liquid from an alkylation process to a liquid-liquid phase separator to separate a flowing liquid hydrocarbon phase from a flowing liquid acid catalyst phase; a liquid flow path for flowing the acid catalyst phase through a flow-through optical cell in optical communication with a spectrometer so that the spectrometer can capture the spectrum of the acid catalyst phase; and a processor that is configured to capture spectra from the spectrometer and is programmed to manipulate each spectrum to determine net responses in the same for the acid ($R_A$) and for water ($R_{H_2O}$) and to determine the weight fractions of acid, water, and hydrocarbons in the acid catalyst phase ($X_A$, $X_{H_2O}$, and $X_{HC}$ respectively) according to the equations $X_{H_2O}=k'''_{H_2O} \cdot R_{H_2O}$, $X_A=k'''_A \cdot R_A$, and $X_{HC}=1-X_A-X_{H_2O}$ where $k'''_A$ and $k'''_{H_2O}$ are parameters determined by calibration based on acid catalyst mixtures whose concentrations of the acid and water, respectively, are known. The acid is typically hydrofluoric acid or sulfuric acid. The processor is typically a general purpose digital computer. In another particular embodiment, the spectrometer is a Raman spectrometer, the optical flow cell is a Raman cell, the net responses in the acid catalyst spectrum for the acid ($R_A$) and for water ($R_{H_2O}$) are the net intensities in the Raman spectrum of the acid catalyst spectrum for the acid and water, respectively. And in another particular embodiment the spectrometer is a near-infrared spectrometer, the optical flow cell is a NIR transmission cell; the net responses in the acid catalyst spectrum for the acid ($R_A$) and for water ($R_{H_2O}$) are, respectively, the net absorbances in the NIR spectrum of the acid catalyst for the acid ($A_A$) and water ($A_{H_2O}$); and the weight fractions of acid, water, and hydrocarbons in the acid catalyst phase ($X_A$, $X_{H_2O}$, and $X_A$ respectively) are calculated according to the equations $X_{H_2O}=k'''_{H_2O} \cdot A_{H_2O}$, $X_A=k'''_A \cdot A_A$, and $X_{HC}=1-X_A-X_{H_2O}$ where $k'''_A$ and $k'''_{H_2O}$ are parameters determined by calibration based on acid catalyst mixtures whose concentrations of the acid and water, respectively, are known.

In another particular embodiment, the instant invention is a component of a system for controlling and optimizing alkylation unit operation by means such as manual adjustment of unit operating parameters by unit operators, Advanced Process Control (APC), Model Predictive Control (MPC), and the like, which use information relating to the composition of acid catalyst and of hydrocarbon streams associated with the alkylation unit, the information being supplied by embodiments of online analyzers described herein, and the controlling and optimizing including but not being limited to (i) determining the operating temperature of an HF rerun tower (the fractionation column in an HF alkylation unit that is used to regenerate (purify) BF from the acid catalyst by separating it from water and ASO through distillation) used to remove water and ASO from the acid catalyst; (ii) the management of sulfuric acid in the contactors of sulfuric acid alkylation units; (iii) adjusting conditions in the deisobutanizer and/or other fractionation units to achieve the desired separation performance, and especially to adjust the purity of isobutene in the isobutene recycle stream; (iv) adjusting unit operating parameters in response to changing feed characteristics and also to produce alkylate product with the desired properties; and (v) maximizing unit operating efficiency by taking into account the value of feed, the octane-barrel value of alkylate, the value of energy required to operate the unit, and also the value and consumption of HF and/or other chemicals used in the alkylation process.

In another preferred embodiment, the invention is any of the aforementioned embodiments for determining the composition of catalyst in an alkylation unit and the addition to a spectrometer in any of the embodiments of one or more additional optical channels, each with an associated optical cell interfaced to a hydrocarbon process stream in the alkylation unit to permit measurement of the spectrum of the process sample flowing therethrough, which spectrum is then analyzed by spectrometric methods familiar to those skilled in the art to provide compositional information, and which stream is selected from a list including but not limited to the isobutane recycle stream, deisobutanizer side-draw and bottoms, other streams flowing into or out of other fractionation columns in the alkylation unit, and the alkylate product. In a particularly favorable embodiment, the compositions of catalyst and hydrocarbon streams are analyzed by means of individual, single-point transmitter-spectrometers (NIR or Raman) mounted on or in close proximity to sampling points for those streams and, as appropriate, sampling systems for each of the streams, the composition values being used to control and optimize the alkylation unit operation.

DETAILED DESCRIPTION OF THE INVENTION

Figure 3:
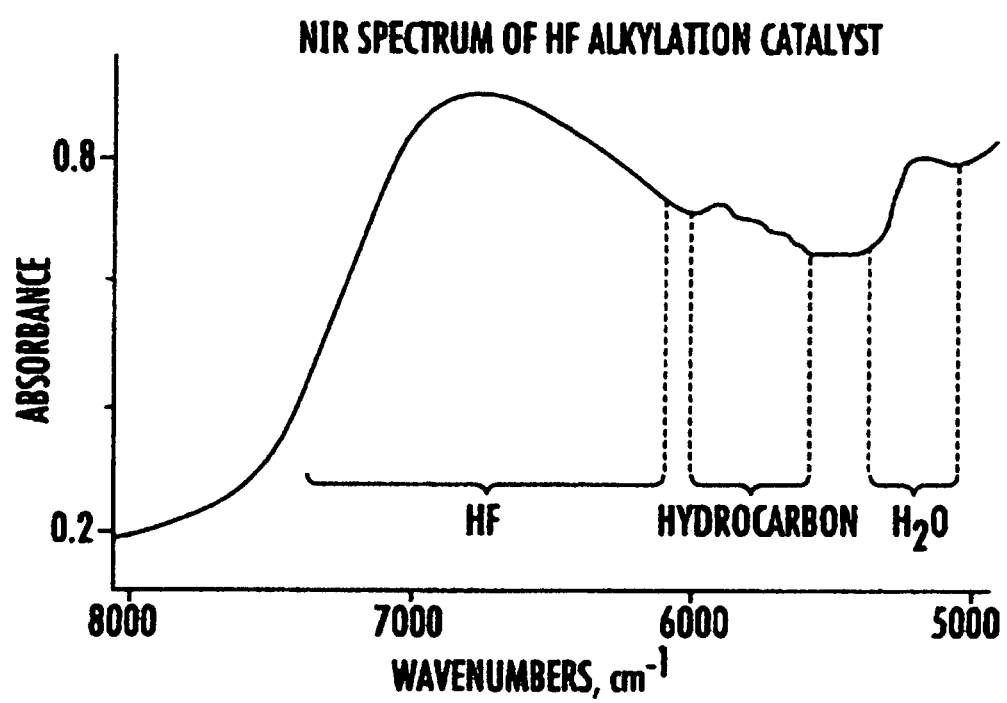
FIG. 3 depicts the NIR spectrum of HF alkylation catalyst.

Problems in prior art on-line analysis of alkylation catalyst will now be discussed. The instant invention represents a novel, non-obvious departure from the prior art by dint of several innovations. First, it permits the analysis of a continuously-flowing sample, whereas the established practice of acid catalyst by NIR spectrometry relies on stopped-flow analysis, i.e. a sample shutoff valve installed downstream from the NIR transmission cell is closed each time the measurement of a sample spectrum is to be performed, the shutoff valve representing a wear element that must be replaced approximately every six months. Also, the instant invention substantially overcomes problems that are inherent in spectral analysis by chemometric means applied in support of catalyst analysis based on spectrometry, e.g. when partial least squares (PLS) is applied to model a chemical system that has only three distinctly different classes of components (acid, water, and hydrocarbons). Though well established and effective for modeling of properties in chemical systems with many degrees of freedom, e.g. octane and other properties in gasoline, difficulties can arise when PLS is applied to systems such as alkylation catalyst, which is dominated by one component (hydrofluoric acid (HF) or sulfuric acid) that effectively functions as a solvent for the other components (water and hydrocarbons), the issue being a system that substantially has two degrees of freedom while multivariate chemometric algorithms such as PLS are in general better suited for more complex systems. Further, the common practice of normalizing spectra by dividing spectral intensities by the total integrated area (area) of the spectrum is especially problematic. Commonly referred to as area normalization, the weakness of this method is that the total area varies substantially as a function of varying levels of the acid, which dominates the catalyst spectrum as FIG. 3 shows is the case for HF catalyst. This means that the very spectral changes that are the basis for quantifying HF in the catalyst are attenuated through area normalization. Additionally, given how absorbance by HF dominates the catalyst spectrum, area normalization will change absorbances associated with water and HC relative to those for HF. Consequently, two catalyst samples with different concentrations of HF, water, and HC could have the same area. Or, the areas for two samples with identical amounts of HF but differing relative amounts of water and HC could be different. The implication of these and other similar scenarios is that predictions by PLS models for the three components will be somewhat erroneous.

Figure 2:
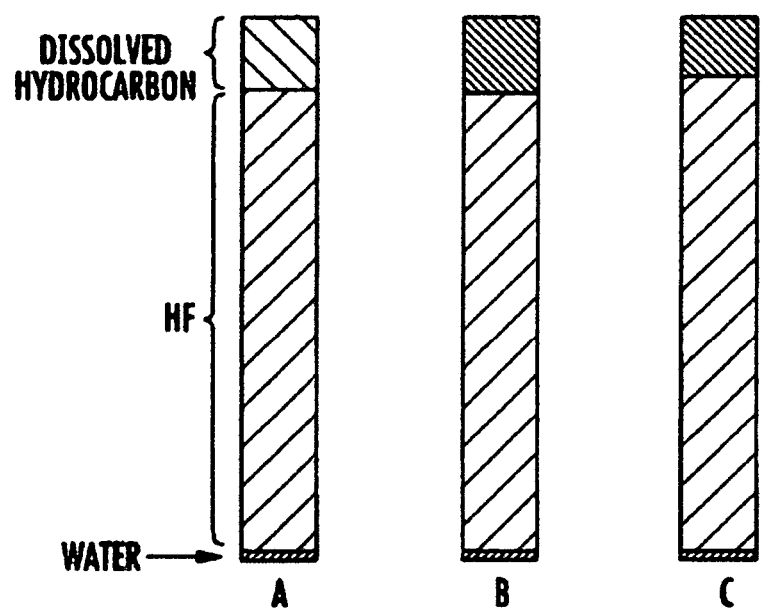
FIG. 2 depicts an illustration of ambiguity caused by variation in the effective in-solution density of hydrocarbons in HF alkylation catalyst.

An additional problem in the prior art is that both the density and absorptivities of the HC vary as a function of the components therein. FIG. 2 illustrates the consequence of this for prior art that relies on a sample's measured density to quantify the relative amounts of HF and HC. The columns labeled A-C depict the relative volumes of HF, water, and HC in three different acid catalyst samples. Samples A and B contain identical volumes of all three. However, the darker shading of the HC portion in Sample B signifies that its HC fraction has higher density that of Sample A. The overall density of Sample A therefore will be lower than that of Sample B, yielding a calculated value for % HF (weight basis) in the latter that is lower even though its volume is the same as in Sample A. But referring now to Sample C in FIG. 2, consider what happens when a sample's HC has the same density as that in Sample B but a lower volume than in either Sample A or B. Compared with Sample B, the overall density of Sample C will be lower. However, the case may arise where the higher density of HC in the former exactly offsets the overall lower volume of HC so that the overall density of Samples A and C match exactly. Because both prior art methods for analyzing alkylation catalyst lack the means to assess and compensate for changing density of HC in a sample, the multivariate models used to infer composition underdetermine the catalyst composition. That necessarily results in prediction errors.

Concerning the multi-sensor strategy, the argument may be made that additional sensor inputs beyond density and conductivity can provide the information required to completely "determine" sample chemistry, with temperature (T) being one such candidate. Conductivity and density respond predominantly to water and the acid-HC ratio, respectively, Notionally, temperature information could be used to compensate for T-dependent changes in density, e.g. for those arising in connection with coefficients of thermal expansion for the major components in acid catalyst, e.g. $(\alpha_V)_A$ or $(\alpha_V)_{HC}$ for the acid and HF, respectively. However, though not wishing to be bound by any particular theory of operation, it is believed that the practical significance of variations in acid catalyst density as a function of temperature and $(\alpha_V)_A$ or $(\alpha_V)_{HC}$ is very low compared with those resulting from changes in the relative amounts of acid or HC in the acid catalyst, or from changes in the in-solution density of the HC fraction that is a consequence of changing proportions of constituent hydrocarbons. Therefore information about HC density must be obtained from a sensor or sensors in addition to those measuring the temperature, conductivity and density of the sample stream.

Alkylation catalyst is in concept a simple ternary solution comprising an acid, water, and hydrocarbons, and the objective of the traditional laboratory method of analysis is to measure the weight fraction of each component, $X_i$. However, the interplay between that parameter, the chemical nature and solution behavior of components in the catalyst, and the physico-chemical measurement principles of online analytical devices apparently has not fully understood by persons who practice the online analysis of alkylation catalyst by prior art. Not wishing to be limited by any particular theory governing solutions comprising HC and water in an acid, the following detailed examination of that interplay reveals two conditions that must be satisfied substantially in order for the prior art approaches to provide a reliable accounting of catalyst composition. Ironically, even though those approaches differ in significant ways, the limitations of both have a common source. It will be understood that although the conditions are presented in absolute terms, they would only need to be satisfied approximately to achieve acceptable analytical reliability by the prior art approaches (analytical errors resulting from deviations from the conditions can be relatively small compared with the requirements of reliable alkylation unit operation). Additionally, although framed in terms of HF alkylation catalyst for clarity, the discussion will be understood as applying equally to catalyst where the acid is sulfuric acid.

Condition 1. Each component's effective in-solution density, $d_i$, must be constant across the measurement range of interest when temperature is constant. As a practical matter, this condition needs to hold across only the relatively narrow ranges for $X_i$ that are important for alkylation unit control and optimization, e.g. from about 82% to about 92% HF or from about 88% to about 98% SA.

Condition 2. In spectrometric techniques, the aggregate intensities of spectral responses per unit mass of a given component (acid, water, or HC) must be constant. This is a core principle of the Lambert-Beer Law, which is the basis for much quantitative spectroscopy and is given by Eq. (4). Even quantitative Raman spectroscopy, which is not based on absorption of light, relies on the signal for a given chemical specie varying as a linear function of its concentration.

Figure 4:
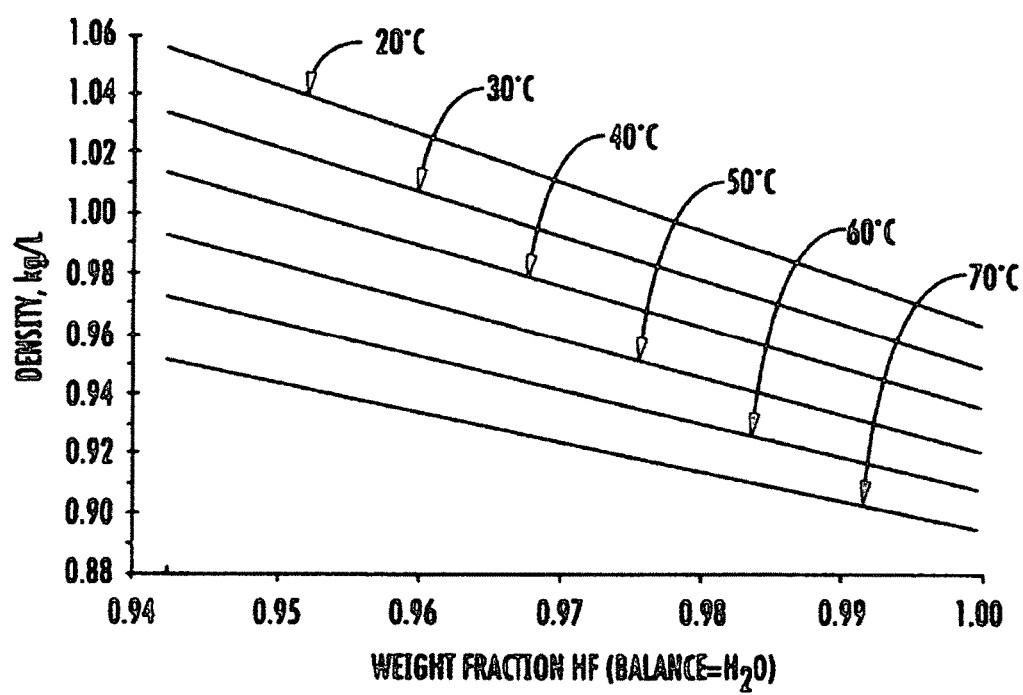
FIG. 4 is a plot of density v. weight fraction HF in HF-water mixtures at various temperatures.

At issue is whether these conditions are satisfied approximately, i.e. deviations do not impair the analytical reliability of prior art methodologies. The scenario described in connection with Samples A and B in FIG. 2 suggests that even if Condition 1 holds for HF and water, it may not hold for HC. Referring now to FIG. 4, it can be seen that $d_{cat}$ varies linearly as a function of $X_{HF}$ in the case where the catalyst is a binary mixture containing only water and HF, suggesting that the in-solution densities $d_{HF}$ and $d_{H_2O}$ are different but approximately constant across the given range of values for $X_{HF}$ and that Condition 1 therefore holds for HF and water. (Water levels in HF alkylation units typically are maintained below about 2.0%.) Similar data is not available for a binary mixture of defined-composition HC in HF. However, supposing that it were, and that analogous plots of density versus $X_{HF}$ were obtained at the each temperature shown in FIG. 4, they would be valid only for HC with a given composition-determined density. Because the isothermal density-versus-$X_{HF}$ relationships would be different if HC density were different, Condition 1 therefore would not hold across all densities for HC.

Turning now to Condition 2, a reasonable assumption can be made that if the in-solution densities of HF and water are conserved across a relevant range of concentrations, then so too will their net spectral response per mole, i.e. the molar absorptivities. In the case of HC, however, two factors obviate this possibility. First, while HF and water are defined chemically, HC is a diverse mixture of components, e.g. isobutane and the compounds in ASO, whose proportions can vary over time in an alkylation unit. Second, the equivalents of different organic functional groups in ASO per unit mass ASO may vary as the composition of ASO varies. Even isobutene is understood to be a mixture of saturated light hydrocarbons, and their aggregate concentration relative to that of ASO is understood to not be constant. In combination, these factors conspire to preclude the possibility that Condition 2 holds across the range of possible compositions for HC in acid catalyst.

More specifically, consider that the amount of light absorbed by each component depends not only on its volume fraction in the mixture, but also its absorptivities at different frequencies interrogated by the spectrometer. And referring now to FIG. 3, consider additionally that in the NIR spectrum of HF catalyst, the expression of HC in the first C—H overtone region (at approximately 5,800 cm$^{-1}$ to 6,000 cm$^{-1}$) is predominantly a function of the amount of C—H chemical functionality contained in the HC. Consider finally the general trend for the amount of C—H functionality per unit mass of HC to decrease as a function of increasing density (e.g. as ASO density increases, H:C decreases). The consequence is that the mass HC per unit absorbance at different frequencies in a spectrum can be highly variable. Referring again to FIG. 2, the preceding facts mean that the net amount of NIR light absorbed per gram of HC in Sample A may be greater than for Samples B and C. Consequently, the aggregate absorbance, e.g. the area, of HC in NIR spectra of Sample A could be greater than that of Sample B, despite the weight-basis concentration of HC in the former being lower. These examples serve to illustrate that variation in net absorbance values in the C—H overtone is not solely a function of weight-basis HC concentration. Yet, the underlying premise of chemometric-based NIR spectrometry is that a unique spectrum yields a unique mathematical solution. The under-determination of sample chemistry by the prior art NIR method means that unique quantitative solutions cannot be obtained from the spectral responses that are the basis for the chemometric prediction of catalyst composition.

Recognizing that the chemical character of ASO can vary as a function of feed composition and operating conditions in the alkylation unit, the potential implications for any online method for analyzing acid catalyst will be understood intuitively by alkylation engineers. Undergirding the idea that ASO chemistry is variable is the historic differentiation by engineers in the field between light and heavy ASO, some even suggesting that light ASO might include alkylate. Clouding the issue further is uncertainty concerning the solution concentration of isobutane, whose density and spectral response is different from those of light and heavy ASO. The in-solution density of low-molecular weight hydrocarbons like isobutane and those in heavy ASO have been estimated to vary from below about 0.7 kg/L to more than about 0.9 kg/L, respectively.

Given that ASO is thought to be merely one of a plurality of subclasses of hydrocarbons in the HF catalyst phase and may itself comprise light and heavy ASO, the term hydrocarbons (HC) is used herein to denote all organic components in the single-phase acid catalyst. For, HC is appropriately viewed as comprising a continuum of chemistries ranging from isobutane to high-molecular-weight compounds in heavy ASO. This being the case, the in-solution density of HC would be expected to depend on 1) the in-solution densities of the different classes of compounds in acid catalyst, and 2) their relative amounts in the HC fraction. The fidelity of all analytical techniques for online analysis of HF catalyst depends on the extent to which they can compensate for variations in both. Yet, prior art depends on the aggregate value for $d_{HC}$ being nominally constant regardless of HC composition, while prior art spectrometric methods depend additionally on spectral responses per unit mass HC being nominally constant.

The following discussion considers the implications of the conditions asserted above for the prior art HF analyzer offerings. Different as are the corresponding technical approaches employed by each, the robustness of measurements by both depends on the effective in-solution density of hydrocarbons, $d_{HC}$, being nominally constant at all times.

Implications for HF analysis based on FTNIR spectrometry. Mark et al. (H. Mark, R. Rubinovitz, D. Heaps, P. Gemperline, D. Dahm, and K. Dahm, Appl. Spectrosc. 64, 995 (2010)) pointed out in an insightful article that quantitative NIR methods involving the absorption of light by liquid samples in a fixed-pathlength transmission cell are volumetric, not mass-based. That article examines the implications for quantitative spectroscopy of the non-linear relationship between volume-percent and weight-percent. Coincidently, the study considers a ternary system which, though different from HF catalyst, provides a helpful analogy.

Mark et al. unfortunately stopped short of making the fundamental observation that a spectrometer counts functional groups (chemical equivalents) per unit volume, the key point being that quantitative FTNIR spectrometry of liquid samples in an optical transmission cell measures equivalents per unit volume rather than equivalents per unit mass. With equivalents being proportional to equivalent mass, then the application of FTNIR spectrometry by means of a defined-volume liquid transmission cell cannot directly measure weight fraction (or weight percent), but only mass per unit volume, which at the root is a density function. The problem is exacerbated by the fact that the FTNIR response relates not to mass, but to C—H equivalents. Consider that the hydrogen-to-carbon ratio can vary from 2.5:1 in butane to less than about 1.4:1 in heavy ASO (equivalent basis). The measurement of HC in HF catalyst depends on C—H absorbance per unit mass HC being constant, which apparently is not possible. The combined variations in the in-solution density of HC and the net molar absorptivity of HC means that conventional FTNIR spectrometry cannot in the limit accurately analyze the composition of HF catalyst for which the in-solution density and spectral responses of HC vary.

Yet another complication, which is beyond the scope of the present discussion but will be understood by those skilled in the art, is the practice of spectral scaling by area normalization. It can be employed to great effectiveness in many NIR applications. However, Martens and Nws (H. Martens, T. Naes, *Multivariate Calibration* (1989), section 7.4.2.1), who describe the method as normalization by closure, advise that it should be applied with caution, as it can have adverse effects in some applications. The NIR analysis of HF catalyst is one such case, as its spectrum is dominated by the major component (HF), the variation of whose spectral response has a dominant influence on the outcome of normalization by closure. (Those skilled in the art will appreciate that although the preceding discussion specifically considers FTNIR spectrometry, the issues apply in equal force to Raman spectrometry, which also has been promoted for the analysis of HF alkylation catalyst.)

Implications for HF analysis with multi-sensor systems. The combining of multiple univariate sensors to create a multivariate analyzer system assumes that their differential responses to each of the components in HF catalyst are distinct, or at least very dissimilar. Because the densities of HF and water are quite similar, conductivity is the principal means for assessing water content whereas changes in the amount of HC relative to the HF/water fraction correlate principally with density. But as has been discussed already, failure of Condition 1 to hold due to variation in the in-solution density of HC limits the possibility to reliably determine the composition of acid catalyst by means of a multi-sensor system that relies principally on density (to assess the relative proportions of acid and HC) and conductivity.

The foregoing discussion establishes that the limiting issue with all prior art is that the analytical strategy underdetermines the chemistry of the catalyst sample. Having recognized this, the inventor of the instant method and apparatus for analyzing alkylation catalyst understood that overcoming the limitations of prior art requires that the amount of information obtained by the analyzer system substantially matches or exceeds the degrees of freedom in the chemical system that is the object of analysis. In the case of HF alkylation catalyst, the variations of greatest importance include % $H_2O$, % HC, and the in-solution densities of HF, $H_2O$, and HC ($d_{HF}$, $d_{H_2O}$, and $d_{HC}$), while the coefficients of thermal expansion of all components in the catalyst (HF, $H_2O$, and HC) are believed to have relatively low importance. Note that although % HF was not included in the preceding list with % $H_2O$ and % HC, it is implied because 100%=% HF+% $H_2O$+% HC. (Expressions of weight percent or volume percent in terms of the three components have only two degrees of freedom, as the sum of the three components is constant when HC is regarded as a single component. The reality is that % HC=100·$\Sigma hc_i$, where each $hc_i$ is the fraction of the catalyst sample corresponding to each of the individual hydrocarbon species in the catalyst or, more generally, to each sub-class of hydrocarbon species that have common densities and C—H absorptivities. The root of the analytical problem is that the determination of $hc_i$ for each component or class of components is, as a practical matter, not possible.)

Heretofore the detailed discussion has focused extensively on problems that impact the analysis of alkylation catalyst and on consequential limitations of prior art approaches. Detailed consideration will now be given to the instant invention, which deals directly with those issues and overcomes those limitations.

Derivation of Eq. (1). The basis for the instant invention is Eq. (1), $$X_{HF} = k_{HF} \cdot \frac{A_{HF}}{d_{cat}} \quad (1)$$

$$X_{H_2O} = k_{H_2O} \cdot \frac{A_{H_2O}}{d_{cat}}$$

Though simple in form, its implications are profound. Also, it was obtained by a derivation which is non-obvious, as will be shown now with reference to Table 1 for the equations of the derivation and to Table 2 for the definition of the variables in those equations. The starting point is Eq. (2), which is definitional and states that on a weight basis, HF, HC, and $H_2O$ account for the entirety of liquid catalyst phase (the catalyst). Eq. (3) offers an expression showing that the weight and volume fraction of the component in the catalyst relates as the ratio of the in-solution density of the $i^{th}$ component to the density of the catalyst sample, $d_i/d_{cat}$. Eq. (4) is a statement of the familiar Lambert-Beer Law, which defines the absorbance due to the $i^{th}$ component in a sample as the product of its molar absorptivity, its concentration, and the pathlength of the transmission cell containing the sample. It will be understood by those skilled in the art of quantitative spectrometry that the molar absorptivity, $\alpha_i$, has a unique value at each wavelength $\lambda_j$ (or frequency) where a component absorbs NIR radiation. Therefore, for clarity this derivation follows the customary practice of not including subscripts to denote this fact, e.g. $(\alpha_i)_\lambda$. Likewise, practitioners of quantitative spectrometry appreciate that $A_i$ can denote either absorbance at a particular wavelength, e.g. $(A_i)_\lambda$, or the integrated area of an absorption band across some defined wavelength range. (Those skilled in the art of quantitative spectrometry will also recognize that although the derivation of Eq. (1) herein invokes the Lambert-Beer Law, a corresponding derivation can be developed based on the linear relationship between the intensity measured in Raman spectra for a particular chemical specie and the solution concentration of the same, e.g. $R_i \propto c_i$, which derivation also would obtain Eq. (1).) Eq. (5) simply shows the relationship between concentration based on moles solute, $c_i$, and concentration based on mass, $c'_i$, while Eq. (6) provides an important expression of $c'_i$ as the product of $X'_i$ and $d_i$.

The next step is the substitution of Eq. (5) into the Lambert-Beer equation followed by the substitution into the resultant equation of $c'_i$ given in Eq. (6) to obtain Eq. (7). Final steps in the derivation of Eq. (1) include rearranging Eq. (7) to obtain Eq. (8) and also Eq. (3) to obtain the equality $X_i \cdot d_{cat} = X'_i \cdot d_i$ (not shown). Substitution of the latter into Eq. (8) followed division of each side of the equation by $d_{cat}$ yields Eq. (9) and the corresponding expressions for HF and $H_2O$ given by Eq. (1).

Deliberately omitted from Eq. (1) is an expression for $X_{HC}$ corresponding to those for HF and water. The reason, of course, is that such an equation would require a constant, $k_{HC}$. Yet, the discussion offered hereinabove suggests that unlike HF and water, the properties of hydrocarbons in the HF catalyst phase may be highly variable. Critically, neither $d_{HC}$ nor the effective absorptivity for HC can be assumed to be nominally constant. Eq. (3) shows that $X_{HC}$ will vary as a function of $X'_{HC}$ and $d_{HC}$ while Equations (8) and (9) show that it also varies with $\alpha_{HC}$.

Therefore, absent viable means for directly determining HC content in acid catalyst, the only practical option for determining catalyst composition is to determine $X_{HF}$ and $X_{H_2O}$ directly and then calculate $X_{HC}$ according to Eq. (10). It has been shown that the instant invention supports this strategy by means of online NIR spectrometry, spectral normalization based on real-time density measurement, and Equation (1). In so doing, it side-steps the practical problems caused by variability in HC composition, which undermines prior art approaches conditioned on the density and/or spectral responses of HC being approximately constant.

TABLE 1

Derivation of Eq. (1).

$$\sum_{i=1}^{n} X_i = X_{HF} + X_{H_2O} + X_{HC} = 1 \quad (2)$$

$$X_i = \frac{V_i}{V_{cat}} \cdot \frac{d_i}{d_{cat}} = X'_i \cdot \frac{d_i}{d_{cat}} \quad (3)$$

$$A_i = a_i \cdot l \cdot c_i \quad (4)$$
$$c_i = c'_i / MW_i \quad (5)$$
$$c'_i = X'_i \cdot d_i \quad (6)$$

$$A_i = a_i \cdot l \cdot \frac{c'_i}{MW_i} \quad (7)$$

$$= \left[\frac{a_i \cdot l}{MW_i}\right] \cdot X'_i \cdot d_i$$

$$X'_i \cdot d_i = \frac{MW_i}{a_i \cdot l} \cdot A_i = k_i \cdot A_i \quad (8)$$

$$X_i = X'_i \cdot \frac{d_i}{d_{cat}} = k_i \cdot \frac{A_i}{d_{cat}} \quad (9)$$

$$X_{HF} = k_{HF} \cdot \frac{A_{HF}}{d_{cat}} \quad (1)$$

$$X_{H_2O} = k_{H_2O} \cdot \frac{A_{H_2O}}{d_{cat}}$$

$$X_{HC} = 1 - X_{HF} - X_{H_2O} \quad (10)$$

TABLE 2

| | Definition of Variables |
|---|---|
| $A_i$ | net absorbance of the $i^{th}$ component in the liquid catalyst phase (the catalyst) at a particular wavelength or wavelengths |
| $a_i$ | absorptivity, $cm^{-1}/(mol/cm^3)$ |
| $c_i$ | concentration of the $i^{th}$ component, $mol/cm^3$, equals (mass (g) of the $i^{th}$ component)/($MW^i \cdot cm^3$) |
| $c'_i$ | weight-basis concentration of the $i^{th}$ component, $g/cm^3$ |
| $d_{cat}$ | density of the catalyst solution, e.g. $g/mL$ |
| $d_i$ | in-solution density of the $i^{th}$ component, e.g. g of the $i^{th}$ component in the volume $V_i$ |
| $k_i$ | an empirically-determined proportionality constant for the $i^{th}$ component |
| $l$ | cell pathlength, cm |
| $MW_i$ | molecular weight of the $i^{th}$ component |
| $V_i$ | volume of the $i^{th}$ component in the catalyst |
| $V_{cat}$ | volume of the catalyst |
| $X_i$ | weight fraction of the $i^{th}$ component in the catalyst |
| $X'_i$ | volume fraction of the $i^{th}$ component in the catalyst, i.e. $V_i/V_{cat}$ |

In a particular embodiment the instant invention determines the weight fractions of HF and $H_2O$ ($X_{HF}$ and $H_{H_2O}$, respectively) in the acid catalyst according to Eq. (1) and the weight fraction of HC ($X_{HC}$) according to Eq. (10), $d_{cat}$ being measured by means of a suitable density sensor and $A_{HF}$ and $A_{H_2O}$ being measured by means of a NIR spectrometer in optical communication with an optical transmission cell, where the density sensor and NIR cell are in the flow path containing the acid catalyst and the $A_{HF}$ and $A_{H_2O}$ are, for example, integrated areas within the NIR spectrum of the acid catalyst corresponding to each component, which spectrum is measured by the NIR spectrometer. As is a common practice in NIR spectrometry, a derivative of the absorbance spectrum, e.g. the first derivative, may be optionally obtained prior to determining the integrated areas corresponding to each component.

In another particular embodiment, NIR spectrometer and its associated optical cell are replaced with an online Raman spectrometer and a suitable optical cell or probe to permit measurement of the Raman spectrum of the acid catalyst phase. Because Raman does not use a fixed-pathlength cell, and the intensity of the measured spectrum can vary as a function of laser power, a suitable method for normalizing Raman spectra must be applied which avoids the shortcomings of normalization by closure discussed previously, which are known to those skilled in the art, e.g. factor-based normalization described in U.S. Pat. No. 5,610,836 having been developed specifically for this purpose. Now, Eq. (1) takes the form of Eq. (11), $$X_{HF} = k'_{HF} \cdot \frac{R_{HF}}{d_{cat}} \quad (11)$$

$$X_{H_2O} = k'_{H_2O} \cdot \frac{R_{H_2O}}{d_{cat}}$$

where $R_{HF}$ and $R_{H_2O}$ are the responses in the Raman spectrum of the acid catalyst corresponding to HF and $H_2O$, respectively. And again, the weight fraction of HC is calculated according to Eq. (10).

The preceding two particular embodiments overcome the problem of variable HC composition that limits prior art approaches by means of a spectrometer for measuring responses in catalyst spectra that are specific to HF and water; a sensor for measuring density of the acid catalyst; and spectral normalization achieved by dividing the measured responses by the measured density. Additionally, they avoid problems associated with prior art methodologies that employ multivariate equations or chemometric models to infer values for % HF, % HC or % ASO, and % $H_2O$, relying instead on first-principle analysis of responses for % HF and % $H_2O$ according to Eq. (1).

In yet another particular embodiment, the instant invention is a system for the determination of sulfuric acid alkylation catalyst composition by means of embodiments of the system described hereinabove, while the calculations also may include the correlation of the position of the single SA-water peak with the SA-water ratio (both the position and the area or the intensity of absorption bands associated with SA can vary as a function of water content).

In another particular embodiment, the instant invention is a component of a system for controlling and optimizing alkylation unit operation by means such as manual adjustment of unit operating parameters by unit operators, Advanced Process Control (APC), Model Predictive Control (MPC), and the like, which use information relating to the composition of acid catalyst and of hydrocarbon streams associated with the alkylation unit, the information being supplied by embodiments of online analyzers described herein, and the controlling and optimizing including but not being limited to (i) determining the operating temperature of an HF rerun tower (the fractionation column in an HF alkylation unit that is used to regenerate (purify) HF from the acid catalyst by separating it from water and ASO through distillation) used to remove water and ASO that accumulate in the acid catalyst; (ii) the management of sulfuric acid in the contactors of sulfuric acid alkylation units; (iii) adjusting conditions in the deisobutanizer and/or other fractionation units to achieve the desired separation performance, and especially to adjusting the purity of isobutene in the isobutene recycle stream; (iv) adjusting unit operating parameters in response to changing feed characteristics and also to produce alkylate product with the desired properties; and (v) maximizing unit operating efficiency by taking into account the value of feed, the octane-barrel value of alkylate, the value of energy required to operate the unit, and also the value and consumption of HF and/or other chemicals used in the alkylation process.

Though the measurement of the catalyst spectrum and density by means of an NIR spectrometer and a density sensor might suggest that the instant invention represents an obvious melding of prior art, such is not at all the case, as will now be established in five points. First, the derivation of Eq. (1), which provides the sanction in first principles for the instant invention and method, is non-obvious, and no prior art practices its application. Additionally, the longstanding practice in multivariate spectrometry is to normalize spectral data sets used in modeling by means of algorithms, which range from the simple "area normalization" and the standard normal variate (SNV) calculation to a variety of vector-based approaches including but not limited to multiplicative signal correction (MSC). Also, as a practical matter, vendors and practitioners of NIR spectrometry favor algorithmic normalization for being less expensive and not requiring additional hardware. Thus, the requirement in the instant invention to base spectral normalization on measurement of catalyst density with a density sensor is non-obvious because it is generally considered to be unnecessary.

Second, the use of density in the instant invention is completely unrelated to its use in prior art as one of a plurality of sensors integrated into a single analyzer system to form a multivariate analyzer. In that approach, density is one parameter among many that are inputs into an equation or system of equations for predicting properties of interest, e.g. % HF, % HC, or % $H_2O$. In chemometric parlance, the inputs are independent variables and the predicted properties are dependent variables. Indeed, the multi-sensor system and method is enabled by chemometrics, the properties of interest being inferred or derived rather than being determined directly through first principles. Such mathematical framework finds exact correspondence in chemometric-based spectrometry where, again, the predicted property values are dependent variables while independent variables are individual values arrayed across the range of frequencies, e.g. absorbance values in NIR spectra or intensity values in Raman spectra, which are inputs into the chemometric model. In aggregate, the discrete readings from each sensor in the multi-sensor system form a "property spectrum" that is analogous to NIR or Raman spectra, though it has far fewer data points. By contrast, in the instant invention, density is not an independent variable, but instead is merely used to scale the independent variables (the absorbance or intensity values in a spectrum). Though its function is exactly analogous to that of other spectral normalization methods cited, it is distinctly different and uniquely suited for purposes of the instant invention.

Third, unlike the prior art, which relies on multivariable chemometric methodology to infer properties of interest, the determination of % HF and % $H_2O$ by the instant invention is accomplished by the two simple algebraic functions given in Eq. (1). These functions are based on first principles, each requiring the input of two discrete variables ($d_{cat}$, and $A_{HF}$ or $A_{H_2O}$) that are measured properties of the sample, and also on two constants ($k_{HF}$ and $k_{H_2O}$), which are simply empirical constants (response factors) determined through a conventional calibration process like that used in many discrete analyzers, e.g. gas chromatography (GC) or simple photometry. However, the derivation of Eq. (1) shows that $k_i$ has its origin in real physical constants. Specifically, Eq. (8) shows that $k_i$ is a function of molecular weight, absorptivity, and pathlength.

Fourth, the practice of prior art relies, in the case of NIR, on the control of sample temperature, whereas the multi-sensor strategy measures sample temperature and then uses it as an independent variable in a multivariable equation or set of equations. Thus, the commercially available chemometric-based NIR spectrometric system is known to enclose the transmission cell and other components of the sampling system in a cabinet designed to ensure that sample spectra are measured under isothermal conditions. The multi-sensor system is known to instead analyze the catalyst as-is without any temperature control, incorporating a temperature reading in the equation or system of equations, ostensibly to compensate for temperature-dependent changes in composition. By contrast, the instant invention neither requires temperature control nor incorporates a temperature reading into its calculations to enable temperature compensation. This is because Eq. (1) accounts for and compensates for all temperature-dependent variation in the analytical system, regardless of whether it originates with variable HC chemistry (density), thermal coefficient of expansion of catalyst components, or shifts in absorption bands for HF or water.

Fifth, commercial designs of prior-art NIR-based HF catalyst analyzers employ a sample shutoff valve (SSO) downstream from the NIR transmission cell, its purpose being to stop the flow of sample through the cell during acquisition of each sample spectrum. It is known that this practice is necessitated by the presence of phase-separated liquid hydrocarbons in the catalyst-containing process stream flowing from the alkylation process to the analyzer sampling system through the so-called sample fast loop. These differ from HC in the acid catalyst, being visible in process liquid flowing through the NIR optical cell as a phase distinct and separate from the acid catalyst phase comprising HF, water and HC. It is also known that even when the SSO is closed, the trapped sample often stratifies in the transmission cell to form two distinct, immiscible phases, e.g. the heavier HF catalyst phase and the lighter hydrocarbon phase, just as oil separates from water. To avoid erroneous readings that would be obtained from a spectrum of such a two-layer sample, the known practice is to automatically qualify the sample spectrum by chemometric methods known to those skilled in the art. If found thereby to be unacceptable due to the detection of excess phase-separated hydrocarbon in the sample cell, the analyzer controller opens the SSO to refresh the sample, then closes it to once again permit the spectral qualification. One serious problem with this approach is premature failure of the SSO, which supports a finite number of open-close cycles. Additionally, alkylation units may occasionally operate in a manner such that amounts of phase-separated hydrocarbon in the process liquid may be elevated for significant relatively long time frames, e.g. during a process upset. Thus, for an MR analyzer system that acquires spectra under stopped-flow conditions, the availability and/or reliability of measurements may be significantly diminished on those occasions when information about catalyst composition may be critical for operating the unit safely and efficiently. Preferred embodiments of the instant invention circumvent this problem entirely by (i) conditioning the alkylation process liquid before analysis by flowing through a liquid-liquid separator (LLS) designed remove phase-separated hydrocarbons from the process liquid arriving through the fast loop, the process liquid comprising a liquid phase consisting primarily of hydrocarbon and a liquid phase consisting primarily of the acid catalyst, which phases are distinct and substantially immiscible; (ii) using an optical cell whose free cross-sectional area across the sample flow-path is sufficiently large to accommodate the entire volume of single-phase acid catalyst flowing out of the LLS while minimizing the pressure drop or the inducing of bubble formation through cavitation; and (iii) acquiring sample spectra for analysis as the average of a plurality of spectra measured on the continuously-flowing acid catalyst phase during a time interval of preferably about 0.25 minutes to about 10 minutes.

Highly Preferred Apparatus

In an exemplary preferred embodiment the instant invention is a method and apparatus for determination of HF alkylation catalyst composition comprising measuring the near-infrared (NIR) spectrum and the density of acid catalyst and performing calculations therewith, where (i) the spectrum and the density are measured by means of, respectively, a density sensor and a transmission cell optically coupled to an NIR spectrometer, both the sensor and the cell being mounted on a panel installed within the boundary of the alkylation unit; (ii) the acid catalyst is a liquid phase contained in alkylation process liquid flowing continuously to the panel from a sample transfer line connected to a sample tap at a point in the alkylation process containing catalyst to be analyzed; (iii) the flow rate of the process liquid flowing to the panel is between about 0.5 and 10 liters per minute; (iv) the process liquid comprises a liquid phase consisting primarily of hydrocarbon and a liquid phase consisting primarily of the acid catalyst, which phases are distinct and substantially immiscible; (v) the first element encountered by the process fluid flowing into the panel is a liquid-liquid separator (LLS) configured to remove liquid phase hydrocarbons in the same and render a single-phase acid catalyst stream for analysis; (vi) the single-phase catalyst phase flows in a downstream fashion through the density sensor and NIR cell, which are communicably coupled in the flow path to each other and to the LLS; (vii) the calculations include (a) optionally obtaining of the first or second derivative of the spectrum, (b) normalization (scaling) of the intensities in the same by dividing into them the sample density measured by the density sensor, and (c) the obtaining of integrated areas from the density-normalized NIR spectrum, which correspond to responses for HF and water; (viii) the purpose of the calculations is to provide values for % HF and % $H_2O$ according to Eq. (1) and for percent hydrocarbon in the acid catalyst phase (HC) according to Eq. (10).

In another preferred embodiment, the instant invention is a method and apparatus applied for determining the composition of sulfuric acid alkylation catalyst composition, where the acid is sulfuric acid (SA) and the method determines responses in the spectrum of SA for SA and water in the catalyst sample based on the correlation of the intensity or intensities of SA-water peak(s) and/or the positions of the same with the SA-water ratio. In yet another preferred embodiment, the acid in either HF or SA and the apparatus includes a Raman spectrometer and associated optical cell integrated into the sample flow path in place of the NIR spectrometer and its associated optical cell.

In another preferred embodiment, the invention is any of the aforementioned embodiments for determining the composition of acid catalyst in an alkylation unit and the addition to a spectrometer of one or more additional optical channels, each with an associated optical cell interfaced to a hydrocarbon process stream in the alkylation unit to permit measurement of the spectrum of the process sample flowing therethrough, which spectrum is then analyzed by spectrometric methods familiar to those skilled in the art to provide compositional information, and which stream is selected from a list including but not limited to the isobutane recycle stream, deisobutanizer side-draw and bottoms, other streams flowing into or out of other fractionation columns in the alkylation unit, and the alkylate product. In a particularly favorable embodiment, the compositions of catalyst and hydrocarbon streams are analyzed by means of individual, single-point transmitter-spectrometers mounted on or in close proximity to sampling systems for each of the streams, the composition values being used to control and optimize the alkylation unit operation.

Figure 1:
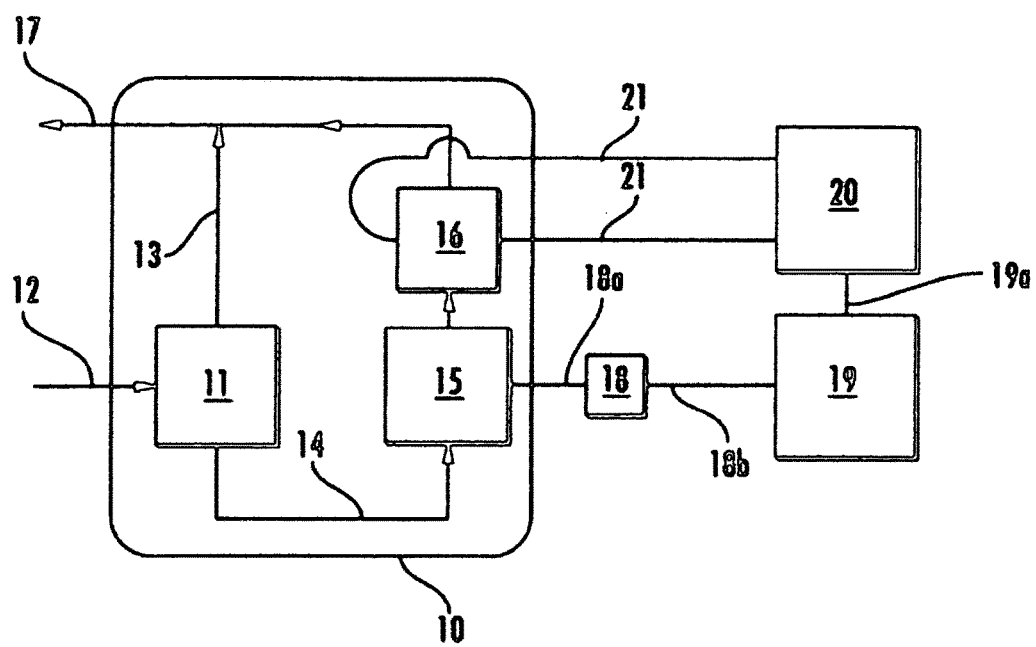
FIG. 1 shows a schematic representation of a highly preferred apparatus embodiment of the instant invention comprising a density detector and a NIR spectrometer.

Referring now to FIG. 1, therein is shown a schematic drawing of a preferred apparatus according to the instant invention, which apparatus includes a panel 10 typically located within or near an alkylation process unit. A liquid-liquid phase separator 11 is mounted on the panel 10, such as the liquid-liquid separator described in U.S. Pat. No. 7,972,863. The liquid-liquid separator 11 receives process stream 12 comprising a phase consisting primarily of hydrocarbon and a phase consisting primarily of acid catalyst, which phases are distinct and substantially immiscible. The output of the liquid-liquid separator 11 comprises a stream of hydrocarbon phase 13 and a stream of acid catalyst phase 14. The stream of acid catalyst phase 14 is flowed through Coriolis density sensor 15, then through a flow-through NIR transmission cell 16 and then combined with the stream of hydrocarbon phase 13 to produce return stream 17. A transmitter 18 for the Coriolis density sensor 15 is in electrical communication with the Coriolis sensor 15 and a general purpose digital computer 19 by way of cables 18a and 18b respectively. The Coriolis density sensor 15 and transmitter 18 are available from Yokogawa Corporation of America as the Rotomass RCCS33 system. The flow-through NIR transmission cell 16 is in communication with NIR spectrometer 20 by way of fiber optic cables 21. The NIR spectrometer 20, cables 21 and flow-through NIR transmission cell 16 are available from Yokogawa Corporation of America as the NR800 FTNIR system. The NIR spectrometer 20 is in electrical communication with the computer 19 by way of cable 19a. The computer 19 and the NIR spectrometer 20 are typically located in a process control room or other suitable building proximate to the apparatus. Alternatively, the NIR spectrometer and computer maybe integrated and configured for field mounting within the alkylation unit. Computer 19 is programmed to control the NIR spectrometer 20 and to process the NIR spectral data to determine $A_{H_2O}$ and $A_{HF}$ or $A_{SA}$ for water and hydrofluoric acid or sulfuric acid, respectively; to receive density inputs from the density sensor; and to calculate $X_{H_2O}$ and $X_{HF}$ or $X_{SA}$ from the measured values of $A_{H_2O}$ and $A_{HF}$ or $A_{SA}$, and of $d_{cat}$ to produce a determination of the acid concentration and the water concentration in the acid catalyst phase 14. The pathlength of the NIR transmission cell depends on the specific application but can range from about 0.5 millimeters (mm) or less to 2 mm, 5 mm or 10 mm or more. The NIR spectrum of acid catalyst used for analysis can be in the range of about 4,800 cm$^{-1}$ to about 8,200 cm$^{-1}$, while in other applications the range can be from about 3,800 cm$^{-1}$ to about 5,500 cm$^{-1}$ or the range can be from about 7,500 cm$^{-1}$ to about 11,000 cm$^{-1}$. A preferred embodiment of the present invention measures the NIR spectrum in the range from about 4,800 cm$^{-1}$ to about 8,200 cm$^{-1}$ through an optical transmission cell with a pathlength of about 1 mm to about 3 mm while in a highly preferred embodiment the pathlength is about 2 mm.

Figure 5:
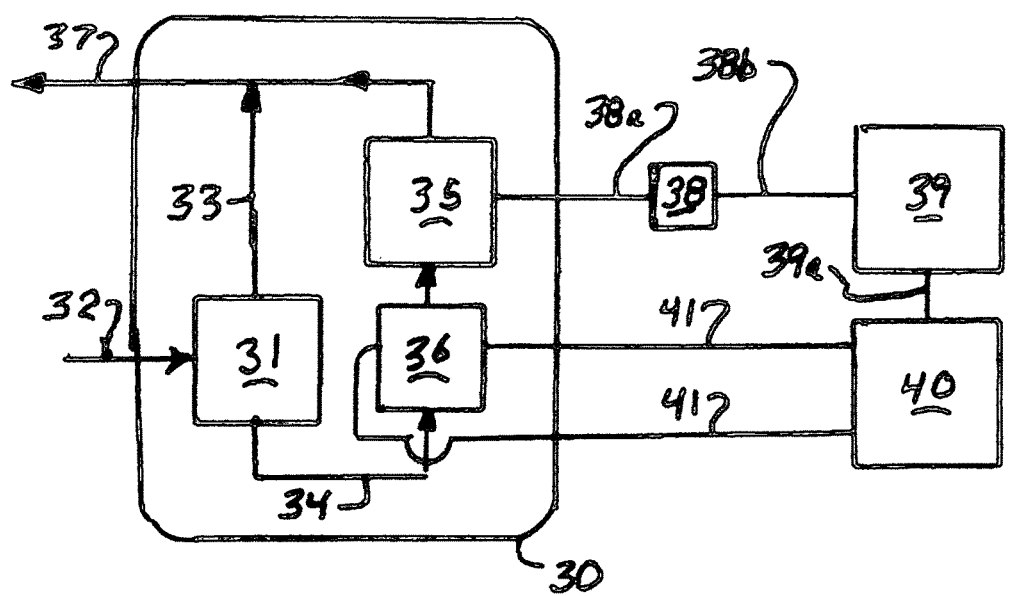
FIG. 5 shows a schematic representation of another apparatus embodiment of the instant invention comprising density detector and a NIR spectrometer.

Referring now to FIG. 5, therein is shown a schematic drawing of another apparatus according to the instant invention, which apparatus includes a panel 30 typically located near an alkylation process unit. A liquid-liquid phase separator 31 is mounted on the panel 30, such as the liquid-liquid separator described in U.S. Pat. No. 7,972,863. The liquid-liquid separator 31 receives process stream 32 comprising a phase consisting primarily of hydrocarbon and a phase consisting primarily of acid catalyst, which phases are distinct and substantially immiscible. The output of the liquid-liquid separator 31 comprises a stream of hydrocarbon phase 33 and a stream of acid catalyst phase 34. The stream of acid catalyst phase 34 is flowed through NIR transmission cell 36 and then through Coriolis density sensor 35 and then combined with the stream of hydrocarbon phase 33 to produce return stream 37. A transmitter 38 for the Coriolis density sensor 35 is in electrical communication with the Coriolis sensor 35 and a general purpose digital computer 39 by way of cables 38a and 38b respectively. The Coriolis density sensor 35 and transmitter 38 are available from Yokogawa Corporation of America as the Rotomass RCCS33 system. The flow-through NIR transmission cell 36 is in communication with NIR spectrometer 40 by way of fiber optic cables 41. The NIR spectrometer 40, cables 41 and flow-through NIR transmission cell 36 are available from Yokogawa Corporation of America as the NR800 FTNIR system. The NIR spectrometer 40 is in electrical communication with the computer 39 by way of cable 39a. The computer 39 and the NIR spectrometer 40 are typically located in a process control room. Computer 39 is programmed to control the NIR spectrometer 40 and to process the NIR spectral data; to determine $A_{H_2O}$ and $A_{HF}$ or $A_{SA}$ for water and hydrofluoric acid or sulfuric acid, respectively; to receive density inputs from the density sensor; and to calculate $X_{H_2O}$ and $X_{HF}$ or $X_{SA}$ from the measured values of $A_{H_2O}$ and $A_{HF}$ or $A_{SA}$, and of $d_{cat}$ to produce a determination of the acid concentration and the water concentration in the acid catalyst phase 14. The pathlength of the NIR transmission cell depends on the specific application but can range from about 0.5 millimeters (mm) or less to 2 mm, 5 mm or 10 mm or more. The NIR spectrum of acid catalyst used for analysis can be in the range of about 4,800 cm$^{-1}$ to about 8,200 cm$^{-1}$, while in other applications the range can be from about 3,800 cm$^{-1}$ to about 5,500 cm$^{-1}$ or the range can be from about 7,500 cm$^{-1}$ to about 11,000 cm$^{-1}$. In another preferred embodiment of the present invention, the range of the NIR spectrum is about 4,800 cm$^{-1}$ to about 8,200 cm$^{-1}$ and the pathlength of the optical transmission cell is between about 1 mm to about 3 mm while in a highly preferred embodiment the pathlength is about 2 mm.

Figure 6:
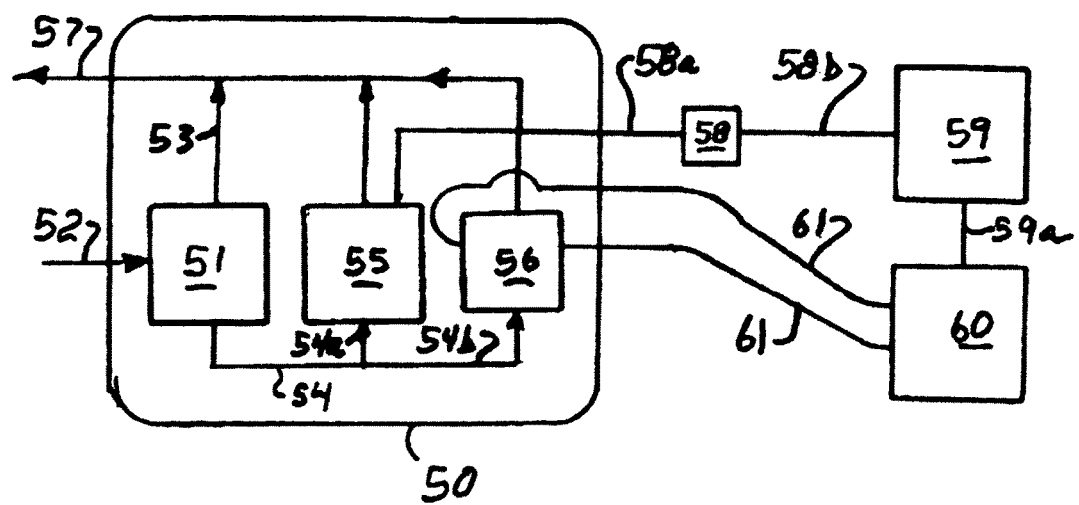
FIG. 6 shows a schematic representation of yet another apparatus embodiment of the instant invention comprising density detector and a NIR spectrometer.

Referring now to FIG. 6, therein is shown a schematic drawing of another apparatus according to the instant invention, which apparatus includes a panel 50 typically located near an alkylation process unit. A liquid-liquid phase separator 51 is mounted on the panel 50, such as the liquid-liquid separator described in U.S. Pat. No. 7,972,863. The liquid-liquid separator 51 receives process stream 52 comprising a phase consisting primarily of hydrocarbon and a phase consisting primarily of acid catalyst, which phases are distinct and substantially immiscible. The output of the liquid-liquid separator 51 comprises a stream of hydrocarbon phase 53 and a stream of acid catalyst phase 54. The stream of acid catalyst phase 14 is bifurcated into streams of acid catalyst phase 14a and flowed through Coriolis density sensor 55 while the stream of acid catalyst phase 14b is through flow-through NIR transmission cell 56. The streams of acid catalyst phase from density sensor 55 and NIR cell 56 are then combined with the stream of hydrocarbon phase 53 to produce return stream 57. A transmitter 58 for the Coriolis density sensor 55 is in electrical communication with the Coriolis sensor 55 and a general purpose digital computer 59 by way of cables 58a and 58b respectively. The Coriolis density sensor 55 and transmitter 58 are available from Yokogawa Corporation of America as the Rotomass RCCS33 system. The flow-through NIR transmission cell 56 is in communication with NIR spectrometer 60 by way of fiber optic cables 61. The MR spectrometer 60, cables 61 and flow-through NIR transmission cell 56 are available from Yokogawa Corporation of America as the NR800 FTNIR system. The NIR spectrometer 60 is in electrical communication with the computer 59 by way of cable 59a. The computer 59 and the NIR spectrometer 60 are typically located in a process control room. Computer 59 is programmed to control the NIR spectrometer 60 and to process the NIR spectral data to determine $A_{H_2O}$ and $A_{HF}$ or $A_{SA}$ for water and hydrofluoric acid or sulfuric acid, respectively; to receive density inputs from the density sensor; and to calculate $X_{H_2O}$ and $X_{HF}$ or $X_{SA}$ from the measured values of $A_{H_2O}$ and $A_{HF}$ or $A_{SA}$, and of $d_{cat}$ to produce a determination of the acid concentration and the water concentration in the acid catalyst phase 54. The pathlength of the NIR transmission cell depends on the specific application but can range from about 0.5 millimeters (mm) or less to 2 mm, 5 mm or 10 mm or more. The MR spectrum of acid catalyst used for analysis can be in the range of about 4,800 cm$^{-1}$ to about 8,200 cm$^{-1}$, while in other applications the range can be from about 3,800 cm$^{-1}$ to about 5,500 cm$^{-1}$, or the range can be from about 7,500 cm$^{-1}$ to about 11,000 cm$^{-1}$. In yet another preferred embodiment of the present invention, the range of the NIR spectrum is about 4,800 cm$^{-1}$ to about 8,200 cm$^{-1}$ and the pathlength of the optical transmission cell is between about 1 mm to about 3 mm while in a highly preferred embodiment the pathlength is about 2 mm.

Highly Preferred Method

Provided here is a general outline of a highly preferred method according to the instant invention covering calibration and subsequent analysis of HF alkylation catalyst.

1. Calibration: Calculation of $k_i$ or $k'_i$ for HF and $H_2O$.
   a. Determine for a plurality of acid catalyst samples values $A_i$ for HF and water where the spectrometer is a NIR spectrometer, or values $R_i$ for HF and water where the spectrometer is a Raman spectrometer, and also $d_{cat}$ for the same samples, where the sample composition spans a range typical of alkylation unit operation.
   b. Determine corresponding values of $X_i$ for HF and $H_2O$ in the same samples, e.g. % HF and % $H_2O$, by means of the standard laboratory method of analysis.
   c. Calculate $k_i$ for HF and $H_2O$ according to Eq. (1) when the spectrometer is a NIR spectrometer, or the corresponding values for $k'_i$ according to Eq. (11) when the spectrometer is a Raman spectrometer. In the former case, $k_i$ is the slope of the line regressed through a plot of $X_i$ versus $A_i/d_{cat}$ whereas in the latter case, $k'_i$ is the slope of the line regressed through a plot of $X_i$ versus $R_i/d_{cat}$.

2. Analysis: Online measurement of $X_i$ for HF and $H_2O$.
   a. Measure the NIR spectrum and $d_{cat}$ on the continuously flowing acid catalyst.
   b. Calculate values $A_i$ or $R_i$, as appropriate, for HF and $H_2O$ from the spectrum.
   c. Calculate $X_i$ for HF and $H_2O$ in the catalyst according to Equations (1) or (11), as appropriate, and for hydrocarbon in the same according to Eq. (10).

In one particular embodiment, the values $A_i$ or $R_i$ are determined on a spectrum that is the average of a plurality of spectra recorded consecutively in a time frame from about 0.25 minutes to about 10 minutes, which sometimes is called the co-added spectrum. A value for $X_i$ is then calculated from these values for $A_i$ or $R_i$ and also from a value for $d_{cat}$ determined from a plurality of consecutive density values acquired in the same time frame as the spectrum. In another embodiment, values $X_i$ are calculated from a plurality of consecutive values for $X_i$, also referred to as a block of $X_i$ values, calculated from a plurality of co-added spectra and corresponding density values acquired in a relatively short time frame of about 0.25 minutes to about 2 minutes. And in a particularly favorable embodiment, the block of values is a moving block encompassing n values for $X_i$ acquired in a continuously advancing time frame that is between about 1 minute and about 10 minutes long.

Alternative Apparatus and Method

Figure 7:
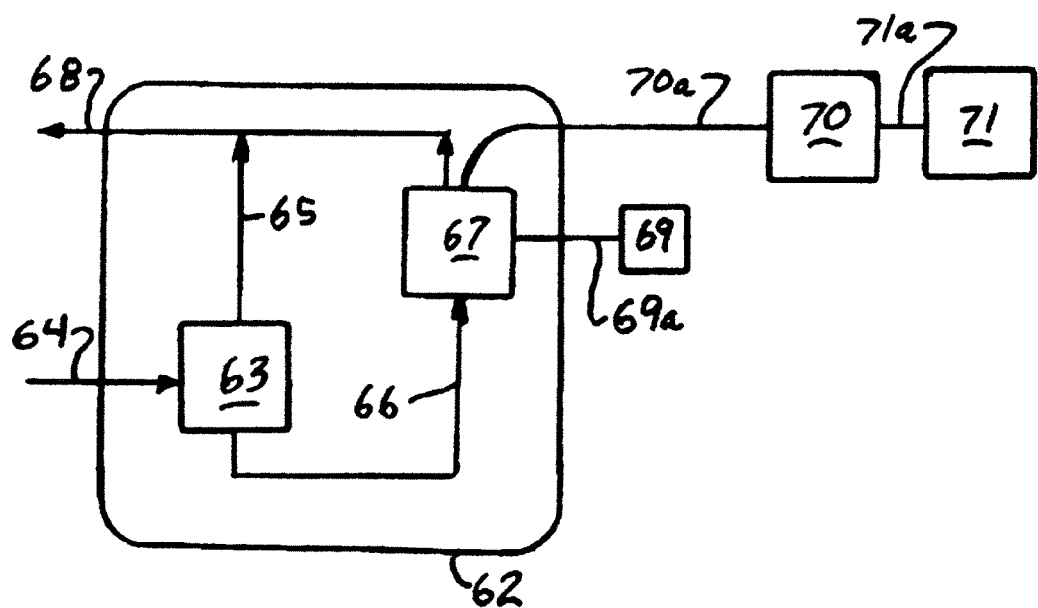
FIG. 7 shows a schematic representation of an apparatus embodiment of the instant invention comprising a Raman spectrometer.

In another embodiment, the instant invention is a system and method that is similar to the above described Highly Preferred Apparatus and the Highly Preferred Method except that the sample interface panel contains no density sensor. Referring now to FIG. 7, therein is shown a schematic drawing of the apparatus, which apparatus includes a panel 62 typically located near an alkylation process unit. A liquid-liquid phase separator 63 is mounted on the panel 62, such as the liquid-liquid separator described in U.S. Pat. No. 7,972,863. The liquid-liquid separator 63 receives process stream 64 comprising a phase consisting primarily of hydrocarbon and a phase consisting primarily of acid catalyst, which phases are distinct and substantially immiscible. The output of the liquid-liquid separator 63 comprises a stream of hydrocarbon phase 65 and a stream of acid catalyst phase 66. The stream of acid catalyst phase 66 is flowed through a flow-through Raman optical cell 67 and then combined with the stream of hydrocarbon phase 65 to produce return stream 68. Raman laser source 69 is in optical communication with the optical cell 67 by way of optical fiber cable 69a. The Raman-scattered light from the cell 67 is directed to Raman spectrometer 70 by optical fiber cable 70a. The Raman spectrometer 70 is in electrical communication with general purpose digital computer 71 by way of cable 71a. Computer 71 and Raman spectrometer 70 are typically located in a process control room while the Raman laser source 69 is typically located near the panel 62.

In this embodiment, the calibration of constants in Eq. (11) and the calculation of $X_i$ by those same equations is performed without density by means of first principles including the determination of responses in Raman spectra of the catalyst for HF and water. Accordingly, Eq. (11) becomes Eq. (12):

$$X_{HF} = k''_{HF} \cdot R_{HF}$$

$$X_{H_2O} = k''_{H_2O} \cdot R_{H_2O} \quad (12)$$

where the $R_i$ denote the Raman responses for the components of interest, Raman being based on a principle other than absorption. In an alternative embodiment, and referring again to FIG. 7, the Raman optical cell 67 is replaced with a NIR transmission cell, the Raman spectrometer is replaced with an NIR spectrometer while the optical fibers 69a and 70a are replaced with fiber optics appropriate for NIR spectroscopy. Now, Eq. (1) becomes Eq. (13):

$$X_{HF} = k'''_{HF} \cdot A_{HF}$$

$$X_{H_2O} = k'''_{H_2O} \cdot A_{H_2O} \quad (13)$$

Regardless of whether the spectroscopy is based on Raman or NIR, this approach of course lacks the important benefit of density-based normalization. In particular, it will be understood that the parameters $k''_{HF}$, $k''_{H_2O}$, $k'''_{HF}$, and $k'''_{H_2O}$ are in fact not constant, but approximations that treat the factor $k_i/d_{cat}$ as if it were constant. In a particular embodiment, values for $k''_{HF}$, $k''_{H_2O}$, $k'''_{HF}$, and $k'''_{H_2O}$ are determined as the slope of a line regressed through data for a population of acid catalyst samples, and as such corresponds to the factor $k_i/d_{cat}$ that would be achieved by dividing $k_i$ by the average density for those samples $\bar{d}_{cat}$. Consequently, deviations in actual $d_{cat}$ from $\bar{d}_{cat}$ manifest themselves directly as errors in calculated values for $X_i$. This alternative embodiment nevertheless represents an improvement over the prior art NIR method, which also makes no provision for the impact of changing HC composition on $d_{cat}$. For example, it offers the benefits of implementation simplicity afforded by the Highly Preferred System and Method, e.g. the acid catalyst is a single phase liquid that is analyzed while flowing continuously through a large-bore optical cell. This in turn obviates the complication and maintenance characteristic of prior art approaches, e.g. that associated with temperature conditioning and use of a sample shutoff valve for stopped-flow analysis. Although the lack of density-based normalization will result in degraded analytical accuracy, it is believed that the accuracy achieved will be substantially the same as that of the prior art NIR method while affording improved operational reliability.

It should be understood that the liquid-liquid phase separator described above is not required in the instant invention if the flow of process stream is interrupted for a time sufficient to permit the hydrocarbon phase of the process stream to separate from the acid catalyst phase with the acid catalyst phase being in the density detector and the NIR cell or in the Raman cell. Such a system is not preferred because it requires one or more valves that complicate system maintenance, e.g. a sample shutoff valve. The term "processor" encompass a data workstation, personal computer, personal digital assistant (PDA), wireless telephone, or any other suitable computing device including a microprocessor, a computer readable medium upon which computer readable program code (including instructions and/or data) may be disposed, and a user interface. The various components of the processor may be localized on one device or distributed between two or more devices. It should be understood that the "processor" of the instant invention is a programmable device that accepts data as input, processes the data according to a stored program and then provides the result as an output. The preferred processor in the instant invention is a general purpose digital computer, which computer is also used to control the spectrometer of the instant invention.

CONCLUSION

While the instant invention has been described above according to several preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains.

What is claimed is:

1. Apparatus for on-line determination of the weight fractions of acid, water, and hydrocarbons in the acid catalyst phase of an alkylation process liquid, the process liquid comprising a liquid phase consisting primarily of the hydrocarbons and a liquid phase consisting primarily of the acid catalyst, said phases being distinct and substantially immiscible, the apparatus comprising: a liquid flow path configured to convey said process liquid flowing from an alkylation process to a liquid-liquid phase separator to separate said liquid hydrocarbon phase from said liquid acid catalyst phase; a liquid flow path for flowing said separated acid catalyst phase through a density detector for measuring the density ($d_{cat}$) of the separated acid catalyst phase and through an optical spectroscopy cell in optical communication with a spectrometer for measuring the spectrum of the separated acid catalyst phase; and a processor configured to capture data from said density detector and spectra from said spectrometer, the processor programmed to manipulate each spectrum to determine net responses in the same for the acid ($R_A$) and for water ($R_{H_2O}$) and to determine the weight fractions in said acid catalyst phase of the acid ($X_A$) according to the equation $$X_A = k'_A \cdot \frac{R_A}{d_{cat}}$$

where $k'_A$ is a constant determined by calibration with acid catalyst mixtures whose concentrations of the acid are known, and water ($X_{H_2O}$) according to the equation $$X_{H_2O} = k'_{H_2O} \cdot \frac{R_{H_2O}}{d_{cat}}$$

where $k'_{H_2O}$ s a constant determined by calibration based on acid catalyst mixtures whose concentrations of water are known, and hydrocarbons ($X_{HC}$) according to the equation $$X_{HC} = 1 - X_A - X_{H_2O}.$$

2. The apparatus of claim 1, wherein the acid is hydrofluoric acid (HF).

3. The apparatus of claim 1, wherein the acid is sulfuric acid (SA).

4. The apparatus of claim 1 wherein the spectrometer is a Raman spectrometer, the optical flow cell is a Raman cell, the net response in the acid catalyst spectrum for the acid ($R_A$) is the net intensity in the Raman spectrum of the acid catalyst for the acid, and the net response in the acid catalyst spectrum for water ($R_{H_2O}$) is the net intensity in the Raman spectrum of the acid catalyst for water.

5. The apparatus of claim 1, wherein the spectrometer is a near-infrared spectrometer, the optical cell is a near-infrared transmission cell, the processor is configured to capture data from the density detector and NIR spectra from said spectrometer and the processor is programmed to manipulate each NIR spectrum to determine net absorbances in the same for the acid ($A_A$) and for water ($A_{H_2O}$) and to determine the weight fractions in said acid catalyst phase of the acid ($X_A$) according to the equation $$X_A = k_A \cdot \frac{A_A}{d_{cat}}$$

where $k_A$ is a constant determined by calibration with acid catalyst mixtures whose acid concentrations are known, and water ($X_{H_2O}$) according to the equation $$X_{H_2O} = k_{H_2O} \cdot \frac{A_{H_2O}}{d_{cat}}$$

where $k_{H_2O}$ is a constant determined by calibration based on acid catalyst mixtures whose water concentrations are known, and hydrocarbons ($X_{HC}$) according to the equation $$X_{HC} = 1 - X_A - X_{H_2O}.$$

6. The apparatus of claim 5, wherein the acid is HF.

7. The apparatus of claim 5, wherein the acid is SA.

8. The apparatus of claim 1, wherein the processor is a general purpose digital computer and wherein the flow-through density detector is a Coriolis density detector.

9. The apparatus of claim 5, wherein the processor is a general purpose digital computer and wherein the flow-through density detector is a Coriolis density detector.

* * * * *

UNITED STATES PATENT AND TRADEMARK OFFICE
CERTIFICATE OF CORRECTION

PATENT NO. : 9,903,810 B2  
APPLICATION NO. : 14/544490  
DATED : February 27, 2018  
INVENTOR(S) : William Marcus Trygstad Page 1 of 1

It is certified that error appears in the above-identified patent and that said Letters Patent is hereby corrected as shown below:

In the Claims

Column 22, Line 11, in Claim 1 after the equation '  ' replace the 's' with a space and the word --is--.

Signed and Sealed this  
First Day of May, 2018

Andrei Iancu  
*Director of the United States Patent and Trademark Office*